United States Patent [19]

Lowicki

[11] 4,172,123

[45] Oct. 23, 1979

[54] DEODORANTS FOR BOTH COSMETIC AND COMMERCIAL USE

[75] Inventor: Norbert Lowicki, Duisburg-Hamborn, Fed. Rep. of Germany

[73] Assignee: Grillo-Werke Aktiengesellschaft, Duisburg-Hamborn, Fed. Rep. of Germany

[21] Appl. No.: 690,204

[22] Filed: May 25, 1976

Related U.S. Application Data

[63] Continuation of Ser. No. 459,814, Apr. 10, 1976, abandoned, which is a continuation of Ser. No. 351,058, Apr. 13, 1973, abandoned, which is a continuation of Ser. No. 842,364, Jul. 16, 1969, abandoned.

[30] Foreign Application Priority Data

Jul. 19, 1968 [DE] Fed. Rep. of Germany ....... 1792074

[51] Int. Cl.$^2$ ................................................ A61K 7/36
[52] U.S. Cl. ......................................... 424/67; 424/65; 424/68; 424/47; 424/76; 424/289; 424/318
[58] Field of Search ..................... 424/65, 67, 76, 317, 424/289, 280, 318

[56] References Cited

PUBLICATIONS

Chemical Abstracts, vol. 60 (1964), p. 11843a.
Chemical Abstracts, vol. 65 (1966), p. 12367a.
Chemical Abstracts, vol. 65 (1966), p. 3635g-h.
Chemical Abstracts, vol. 52 (1958), p. 14957e.

*Primary Examiner*—V. D. Turner
*Attorney, Agent, or Firm*—Sprung, Felfe, Horn, Lynch & Kramer

[57] ABSTRACT

Compositions and processes comprising certain metal salts of an unsaturated hydroxy carboxylic acid having 17–21 carbon atoms are disclosed as the active ingredient in various deodorants. Also described are various synergistic agents, anti-oxidants and reinforcing agents which are useful therewith.

82 Claims, No Drawings

DEODORANTS FOR BOTH COSMETIC AND COMMERCIAL USE

This is a continuation of application Ser. No. 459,814, filed Apr. 10, 1976, now abandoned which, in turn, is a continuation of Ser. No. 351,058, filed Apr. 13, 1973, now abandoned, which, in turn, is a continuation application of Ser. No. 842,364, filed July 16, 1969, now abandoned.

This invention relates to deodorants for both cosmetic and commercial use.

In view of man's increasing sensitivity to unpleasant odours, new substances have been proposed which either prevent the occurrence of unpleasant odours or improve or remove existing odours. Bacteria and fungi are involved in certain decomposition processes which lead to bad odours, and bactericidal and fungicidal agents can prevent such odours by acting as disinfectants and restricting the multiplication of bacteria and fungi and hence the onset of decomposition. This category includes, for example, in the field of cosmetics, hexachlorophene, Raluben and Bidiphen. Odours which already exist, however, are not affected by these materials.

In order to improve existing odours, volatile substances which in most cases have a pleasant odour and are relatively cheap are extensively used, and these mask or improve unpleasant odours from chemicals, technical preparations and the like, even when used in small quantities. Such materials are employed, for example, in petroleum products of various kinds, in air fresheners, lacquers and in rubber goods.

If it is desired not only to mask or improve existing odours but also to remove them, compounds such as n-lauroylmethacrylate, which has been proposed for air freshening, can be used. Here the substances causing the odour are bonded by complex formation, with hydrogen bridges, vinyl groups, dipole forces and Van der Waal forces supposedly being effective. Such materials are not suitable, however, for use in cosmetic or pharmaceutical preparations.

Two approaches have hitherto essentially been used in cosmetic deodorants, namely the inhibition of the exudation of perspiration, and disinfection of the skin. Perspiration-inhibiting substances exert a tanning action on the skin and thus prevent perspiration. Such active substances are mainly aluminum compounds, both of inorganic and of organic nature, optionally combined with sodium compounds. Inorganic compounds of this nature are aluminum chlorides of varying basicity, and purely organic complex compounds of aluminium are for example mentioned in U.S. Pat. No. 3,030,274. In this context, the aluminium salts or sodium-aluminium salts of organic acids, which are optionally also halogenated, are most commonly used (German Auslegeschrift No. 1,122,221).

Analogous zirconium compounds, in part also together with alkali, have also been proposed and described, for example, in U.S. Pat. No. 2,732,327, the preparation of perspiration-inhibiting preparations from these compounds being described in U.S. Pat. No. 2,889,253. As organic acid residues for all these compounds, lactic acid or chlorinated lactic acids as well as stearic acid are almost exclusively mentioned.

The use of zinc compounds or zinc salts is also frequently mentioned, as by, for example, von Schrumpf in his "Textbook of Cosmetics" (W. Mandrich-Verlag, Vienna, 1964). He describes zinc lactate, zinc acetate, zinc phenolsulphonate, zinc salicylate, zinc tannate as well as zinc dimethyldithiocarbamate as mild astringents for this purpose. Zinc undecanoate, optionally together with magnesium undecanoate, has also been mentioned in cosmetics because of its astringent action, which is, however, less irritating to the skin than that of the corresponding aluminium salts (German Patent Nos. 601,474 and 633,661).

A very recent proposal (Janistyn, Pocketbook of Modern Perfumery and Cosmetics, Stuttgart 1966) mentions the zinc compounds described above only as cosmetic auxiliary substances, and quotes only zinc-4-phenolsulphonate as a zinc compound amongst the deodorising active substances.

The suppression of transpiration by skin-tanning substances, for example aluminium compounds, is known to have a very unfavourable effect on the general function of the skin and is only tolerated without irritation for a limited time, if at all.

The various chlorinated hydrocarbons which are mainly used in present day commercially available deodorant preparations are, because of their action, for practical purposes disinfectants the action of which relies on the killing of perspiration-decomposing bacteria. This most commonly followed second approach to deodorising, namely disinfectant, still presents problems. Admittedly it is possible to prevent the biological oxidation processes by killing all micro-organisms, but the bacterial flora intrinsic to the skin can thereby be damaged to such an extent, or even destroyed, that the function of the skin suffers from the long-term use of such preparations. Thus, for example, the fermentation of fatty acids of the skin is stopped as a result of the absence of the bacterial flora killed by the disinfectant and pathological skin reactions can thereby be provoked.

It has been found that new active substance systems which not only open a completely new approach to the mild deodorisation of transpiring sections of the skin in the field of cosmetics, but, because of their long-lasting and strong effect on the one hand and their easy accessibility on the other, can also effectively be used in the most diverse fields of commercial technology. For the cosmetic field it is at the same time of great importance that active substances or active substance mixtures can develop a specific fungistatic activity, whereby odour-forming decomposition reactions which are based on the activity of fungi can be prevented without at the same time interfering with bacterial life processes. Components with unpleasant odour properties which are either produced or already present are effectively absorbed. The new active substances or active substance mixtures at the same time do not only bind organic substances of low molecular weight which have a strong odour, for example, mercaptans, amines, thioethers and the like, but also scents of complex composition. The new materials, which are furthermore distinguished by tolerance by the skin, are thus suitable both for the field of deodorising in cosmetics and also for the prevention of the formation, or for the destruction, of odours of vegetable and animal origin, for example in animal stables, factories processing vegetable and animal products, for example in the fish-processing industry, as well as in household and in technical use.

The present invention is based on the observation that salts especially salts which are sparingly soluble or insoluble in water, of higher carboxylic acids which are both unsaturated and substituted by at least one hydroxyl group are outstanding materials for the desired purpose.

The present invention accordingly provides materials with an odour-binding and, at times, a fungicidal effect, which contain sparingly water-soluble or water-insoluble salts of unsaturated hydroxylated carboxylic acids having at least 17 carbon atoms.

The above carboxylic acids, in general, form water insoluble or sparingly soluble compounds with polyvalent metal cations, for example bivalent or trivalent cations. Suitable metal ions in this respect are those that do not catalyze the decomposition reactions of higher carboxylic acids, as is, for example, known for metals of the nature of iron, copper or nickel. A second aspect as regards the choice of the cations in the active substances according to the present invention is that they should be physiologically harmless. Alkaline earth metals are, therefore, preferably used, especially magnesium and calcium, as well as aluminum and above all zinc. The zinc salts show a pronounced fungistatic activity and are therefore especially important in fields of application in which fungal reactions are to be interrupted, for example, in the field of cosmetics of humans and animals.

The anions of the salts are derived from higher carboxylic acids which are unsaturated, preferably singly or multiply olefinically unsaturated, and show single or multiple hydroxylation. Suitable carboxylic acids are those having from 17 to 21 carbon atoms, preferably from 17 to 19 carbon atoms. These compounds are, in general, relatively inaccessible, which means that those unsaturated, hydroxylated carboxylic acids having 17 or more carbon atoms which are accessible are preferably used. These are primarily higher unsaturated, hydroxylated fatty acids. The most important naturally occurring member of this group is ricinoleic acid. The reaction products obtainable by hydroxylation of fatty acids with multiple unsaturation, for example, linoleic acid and linolenic acid, can however also be used. It is a relatively simple process to hydroxylate one of the two double bonds of this doubly olefinically unsaturated carboxylic acid by a mild oxidation treatment, so that doubly hydroxylated carboxylic acids which are still unsaturated are produced. These and similar carboxylic acids are especially important in the present invention.

The most important salts are the salts of zinc, magnesium and aluminum, of ricinoleic acid, ricinelaidic acid, dihydroxyoctadecane-acid, which may be easily obtained from linoleic acid, as well as the appropriate salts of carboxylic acids with multiple hydroxylation and single multiple unsaturation obtained from the oxidation of linoleic acid.

Zinc ricinoleate is a readily accessible compound and is therefore preferably used in the present invention. It possesses practically no residual astringent action, so that an irritant action on the skin is completely absent. The zinc ion, especially in interaction with the hydroxyl groups simultaneously present, exerts a mild fungistatic effect so that the formation of biological metabolism products which in part cause the decomposition of perspiration constituents and the formation of unpleasant-smelling substances by fermentation is greatly restricted or entirely prevented. The presence of hydroxyl groups as well as the unsaturated character of the acid residue result in a partly absorbent, partly chemical predominantly complex-like binding of the protein-degrading and fat-degrading enzymes, so that an extremely good overall deodorising effect, which starts immediately and which lasts a long time is achieved.

The durability of the deodorants is reinforced by the very good adhesion of practically water-insoluble salts to the skin. There is no danger of their being rubbed off on clothing or rinsed away by exudation of perspiration. A further favourable factor as regards the long-lasting duration of the effect is the very low vapour pressure of the compounds mentioned, so that diffusion loss as a result of body warmth is practically excluded.

It has also been found that the specific properties of zinc ricinoleate and of the other compounds which may be used in the present invention can by synergistically reinforced by the combined use of compounds of a second class. These synergistically active compounds, which are also sparingly water-soluble or water-insoluble, are compounds of carboxylic acids having multiple hydroxylation and a large number of high carbon atoms. Carboxylic acids having from 13 to 21 carbon atoms, preferably from 15 to 19 carbon atoms are especially suitable. Carboxylic acids having at least 17 carbon atoms are especially preferred. These carboxylic acids with multiple hydroxylation can be saturated in nature, but compounds which are accessible in practice are preferred. Compounds which are relatively easily accessible are the oxidation products of unsaturated fatty acids such, for example, as oleic acid, ricinoleic acid, linoleic acid and linolenic acid. Oleic acid on mild oxidation leads to dihydroxystearic acid, rincinoleic acid leads to trihydroxystearic acid and more high unsaturated acids lead to correspondingly more highly hydroxylated products.

Especially important are aleuritic acid (trihydroxypalmitic acid), dihydroxystearic acid (from oleic acid), trihydroxystearate acid (from ricinoleic acid), tetrahydroxystearic acid (from linoleic acid) as well as completely hydroxylated products from more highly unsaturated carboxylic acids, for example from linolenic acid.

These acids are, according to the present invention, preferably used in the form of their salts of the metals specified above and, especially, as their esters.

These compounds, especially trihydroxystearic acid, possess a pronounced synergistic effect in binding odours when mixed with the first-mentioned class of substances. These synergistic agents need not however, be saturated in nature. They can also be unsaturated, especially singly olefinically unsaturated.

The zinc salts of these synergistic agents show excellent tolerance when used on the human body, so that even strongly allergic subjects tolerate the active substance mixture without irritation. The normal fat metabolism of the skin is in no way impaired, so that, in this respect also, there is no danger of skin irritations following prolonged use.

These synergistic agents are, however, preferably esters of the specified higher carboxylic acids. The esters of these acids with monohydric alcohols are especially preferred, the esters of lower alcohols, especially those having from 2 to 6 carbon atoms, being especially suitable.

The compositions according to the present invention therefore include active substance mixtures which contain one or more sparingly soluble or insoluble salts of unsaturated hydroxylated carboxylic acids having at least 17 carbon atoms. In such mixtures, salts mutually support their effect in a synergistic manner. The use of such mixtures of the main class of active substances is however not necessary. The use of only one compound from the main class of active substances, mixed with other compounds from the class of synergistic substances, also leads to the desired boosting of the effect.

Examples of such unsaturated carboxylic acid compounds with multiple hydroxylation which do not fall within the definition of the main class of active substances are esters of the unsaturated higher carboxylic acids with multiple hydroxylation.

It is important that the synergistic effect is apparent when only small quantities of the synergistic agent are present. It has been found that quantities of about 0.5 to about 10% by weight, relative to the total mixture, of synergistic compounds lead to a considerable boosting of the effect in destroying odours. It is preferred, however, to employ active substance mixtures which, relative to the total mixture, contain from 1 to 5% by weight of the synergistic agent in addition to the main active substance.

A further synergistic boosting of the effect, is possible through the use of a third class of substances. Here inter-relations between the components evidently appear to exist, which have a favourable effect both on the odour-suppressing action in itself and also on the duration of the effect. Such a material mixture of all components also leads to a suppression of the inherently unpleasant intrinsic odour of the ricinoleic acid compounds. Such compounds are salts of partially hydrogenated phenanthrene derivatives, especially salts of carboxylic acids of the diterpenes. Examples of this class of substances which are relatively easily accessible in practice are the salts of abietic acid and/or of laevopimaric acid. The salts of these acids with alkaline earth metals, aluminium and, especially, zinc ae especially suitable. These compounds not only boost the prevention or destruction of odours achieved with mixtures of the above described compounds, but also boost the adhesive properties. This second synergistic agent is preferably used in small quantities, for example, from about 1 up to 30% by weight, preferably from about 3 to about 10% by weight, relative to the total mixture. Compounds of the first and second groups of synergistically active substances described above may be obtained in an especially simple manner by working-up tall oil, especially purified tall oil. Tall oil contains a mixture of carboxylic acids which fall within the first and second groups of synergistic compounds and it is therefore possible to obtain a mixture of such compounds from tall oil, after removal of the material which is insoluble in petroleum ether and the material which is unsaponifiable. Tall oil consists of from 35 to 40% of resin acids, predominantly abietic acid, $C_{20}H_{30}O_2$ and from 65 to 60% of fatty acids, predominantly oleic acid, linoleic acid and linolenic acid. Careful oxidation of the alkali soaps of this mixture with $KMnO_4$ and subsequent esterification of the free acids or precipitation of the desired salts produces a mixture of esters or salts of resin acids and hydroxy-fatty acids, which contains synergistic substances of the first and second groups. If a hydroxylated unsaturated fatty acid compound of the main class of active substances according to the present invention, for example a salt of ricinoleic acid, is then further added, an effective mixture of substances can be obtained.

An oxidative degradation of the organic acid residues, which could lead to the formation of subsequent products which themselves have an unpleasant odour can, according to the invention, easily be countered by the addition of a reducing agent. The choice of reducing agent depends on the subsequent use of the composition. Whilst for purely technical uses small quantities of a mild technical reducing agent can be used, the use of skin-tolerated reducing agents of the nature of ascorbic acid, especially in the form of its compounds, for example as 6-palmitoyl-ascorbate or as lauroyl-ascorbate, has proved successful especially in the field of cosmetics. An addition of $\alpha$-tecopherol or of combinations derived therefrom has also proved especially advantageous. The reducing agent is generally present in amounts of less than 1% by weight. Amounts of from 0.05 to 0.2% by weight relative to the total mixture are, for example, especially suitable.

In the cosmetic field, the new active substance mixtures can not only be used in the conventional deodorising preparations such as powders, sticks and sprays, including materials for the care of intimate areas, but the new active substance can also be successfully employed in skin care materials such as soaps, creams, skin milk, foot care materials and hair care materials. In the field of hair cosmetics especially, it is important that on the one hand nocardien are not attacked, whilst on the other hand the zinc content does not impair the sulphhydryl reaction for the synthesis of cystine and hence ultimately the keratinisation, but evidently even assists it.

The fungistatic effect of the new active substance mixture, which especially exists if zinc is present as the cation of at least one of the active substance constituents, can be utilised in various ways. If the cosmetic preparation only contains a restricted quantity of the active substance mixture, for example amounts of from 0.5 to 20% by weight, the deodorising character of the composition predominates. The new occurrence of substances of unpleasant odour is in part prevented, whilst in part newly arising substances of unpleasant odour are immediately bound as they are produced. If, however, the concentration of the active substance mixture according to the invention in the special cosmetic product is increased, preparations are obtained which not only have a strong deodorising action but also exhibit a pronounced fungistatic effect and can, for example, be employed for combatting foot fungus and similar fungal infections. Here concentrations of about 5%, preferably from about 50 to 60%, of the active substance are, for example, suitable.

The odour-binding action which binds even strong odours such as, for example, the odour of herring pickle and the complete tolerance by skin of the material according to the invention makes it possible to use the new materials, alongside their use in the cosmetic and dermatological field, for example in veterinary medicine and in animal hygiene, for example, in caring for domestic animals which are kept in living rooms, or for suppression of odours which can under certain circumstances cause animals to take fright.

A further field of application is the deodorising impregnation of textiles, such as clothing and laundry, and of cellulose articles, for example diapers and materials used for female monthly hygiene. In all these cases the high adhesion of the active substances according to the invention, especially also to fibres of natural and synthetic origin, is again of particular importance for their commercial utilisation. The active substance mixtures according to the invention can also be employed as deodorising washing agent components which are absorbed on the fibres during the washing process. Further fields of use are, for example, materials used in the maintenance of rooms such as waxing compositions and polishes and paints. The use in air fresheners, for example room sprays, as well as for the deodorising of large spaces, for example stables, processing factories for vegetable and animal products, such as fish processing factories and the like is also possible. The strong odour-binding properties also make the use for binding odours in waste substances appear interesting.

The following describes some examples of the manufacture of the active substance components according to the present invention and of some active substance mixtures.

1. Manufacture of Zinc Ricinoleate 25 l of commercial pure castor oil are saponified in a known manner by adding 7.8 l of 38% strength sodium hydroxide solution and 40 l of water in portions. 12.5 kg of zinc sulphate heptahydrate DAB$_6$, dissolved in water to give a volume of 25 l, are added to the clear sodium ricinoleate solution at about 80° C., and the mixture is thoroughly stirred and thereafter allowed to settle. The zinc soap is separated from the mother liquor and poured hot into moulds, where it solidifies.

2. Manufacture of Trihydroxystearic Acid

The solution of sodium ricinoleate obtained according to 1) is acidified with sulphuric acid to pH 2, whereupon the fatty acids of castor oil separate out. 3.0 kg of this acid are saponified with 3.45 l of potassium hydroxide solution, $\rho$ 20° 1.27=28.29% by weight, and 100 l of water. 3 kg of KMnO$_4$ in 200 l of water are introduced into the cold clear potassium soap solution whilst cooling. The potassium soap solution of the trihydroxystearic acid is freed of the hydrated manganese oxide by filtration.

The zinc salt can be precipitated from the clear solution as under 1), 1.45 kg of ZnSO$_4$. 7H$_2$O DAB$_6$ in 10 l of water being required for this purpose. The alkaline earth salt can be precipitated in the same manner. The free acid is separated out at pH 2 by acidifying with H$_2$SO$_4$.

3. Manufacture of Trihydroxystearic Acid Ethyl Ester 3 kg of trihydroxystearic acid are suspended in 10 l of absolute ethanol. Hydrogen chloride gas is slowly introduced at room temperature whilst stirring, until the acid has almost completely dissolved. The alcoholic ester solutionh is freed of a slight residue by filtration; thereafter the ester is precipitated by pouring the alcoholic solution into a 10-fold volume of water. The ester is filtered off and dried. The excess ethanol is recovered from the filtrate by distillation.

4. Manufacture of Ricin-Elaidic Acid

The castor oil acids from 50 kg of castor oil, obtained according to (1) and (2), are warmed in the crude state with 20 l of 50% strength HNO$_3$ (50°–60°). A solution of 1.2 kg of sodium nitrite in 15 l of water is run in whilst stirring well, and the mixture is kept at 50°–60° C. for a further 10 minutes and then rapidly cooled, for example by pouring it onto ice. The reaction product separated from the aqueous phase can be further processed in the crude state like castor oil acid; the pure ricinelaidic acid is obtained by extracting the reaction product with boiling ligroin and crystallizing out by cooling.

5. Manufacture and Dihydroxy-Octadecene-Acid 2.8 kg of linoleic acid are saponified with 3.45 l of potassium hydroxide solution, $\rho_{20}=1.27$, and 100 l of water as described under (2), thereafter oxidised with 3 kg of KMnO$_4$ in 200 l of water with good cooling, and further processed as described above.

6. Manufacture of Tetrahydroxystearic Acid

The manufacture is effected as under (5), except that 6 kg of KMnO$_4$ in 200 l of water are used to oxidise the potassium soap from 2.8 kg of linoleic acid.

7. Working up Refined Tall Oil

The refined tall oil freed of material insoluble in petroleum ether and of unsaponifiable material is saponified according to (2) with aqueous potassium hydroxide solution to give a clear potassium soap solution and is oxidised with dilute KMnO$_4$ solution. From the soap solution which has been clarified by filtration, it is possible either to precipitate the corresponding Zn, Al or alkaline earth salts as such according to (1) or to precipitate active substance mixtures of appropriate composition after mixing the soap solution with alkali ricinoleate solutions. It is however also possible to obtain the free acids by acidifying the potassium soap solution with sulphuric acid to pH 2, and to esterify these after purification according to (3).

The amounts of potassium hydroxide solution for the neutralisation and of KMnO$_4$ for the oxidation depend on the composition of the refined tall oil and on the desired degree of oxidation of the unsaturated fatty acids.

Active Substance Mixture A 95 parts of zinc ricinoleate
3 parts of zinc abietate
2 parts of zinc hydroxystearate and
0.05 parts of 6-palmitoyl-ascorbate, manufactured by the conjoint saponification of castor oil and colophony balsam resin WW, addition of potassium trihydroxystearate and conjoint precipitation of the zinc salts with zinc sulphate heptahydrate DAB$^6$, and addition of the antioxidant to the liquid organic phase.

Active Substance Mixture B 95 parts of zinc ricinoleate
3 parts of zinc abietate
2 parts of trihydroxystearic acid ethyl ester and
0.05 parts of $\alpha$-tocopherol, manufactured by conjoint saponification of castor oil and balsam resin WW and addition of the trihydroxystearic acid ethyl ester as well as of the antioxidant to the liquid organic phase.

Active Substance Mixture C 50 parts of zinc ricinoleate
45 parts of zinc ricinelaidate
3 parts of zinc abietate
0.1 parts of lauroyl-ascorbate and
2 parts of tetrahyroxystearic acid ethyl ester, manufactured by conjoint saponification of castor oil and balsam resins WW, addition of sodium ricinelaidate, conjoint precipitation of the zinc salts and addition of tetrahydroxystearic acid ethyl ester and lauroyl-ascorbate to the liquid organic phase.

Active Substance Mixture D 92.9 parts of zinc ricinelaidate
5 parts of zinc abietate
2 parts of tetrahydroxystearic acid ethyl ester and
0.1 parts of α-tocopherol,
manufactured by conjoint precipitation of the zinc salts from the solutions of the alkali salts and addition of the tetrahydroxystearic acid ethyl ester as well as of the antioxidant.

Active Substance Mixture E 92.9 parts of zinc ricinelaidate
3.5 parts of magnesium abietate
3.5 parts of magnesium aleuritinate and
0.1 parts of 6-palmitoyl-ascorbate,
manufactured by conjoint precipitation of the magnesium salts and addition of these as well as of the antioxidant to the zinc ricinelaidate.

Active Substance Mixture F 50 parts of zinc ricinoleate
40 parts of zinc ricinelaidate
2 parts of zinc abietate
5 parts of aleuritic acid ethyl ester
3 parts of trihydroxystearic acid ethyl ester and
0.05 parts of α-tocopherol,
manufactured by conjoint saponification of castor oil and balsam resin WW, addition of sodium ricinelaidate, conjoint precipitation of the zinc salts and addition of the esters as well as of the antioxidant.

Active Substance Mixture G 50 parts of zinc ricinoleate
45 parts of zinc dihydroxyoctadecenate
3 parts of zinc abietate
2 parts of tetrahydroxystearic acid ethyl ester and
0.1 parts of α-tocopherol,
manufactured by conjoint saponification of castor oil and balsam resin WW, addition of potassium dihydroxyoctadecenate, conjoint precipitation of the zinc salts and addition of tetrahydroxystearic acid ethyl ester and antioxidant.

Active Substance Mixture H 50 parts of zinc ricinoleate
45 parts of magnesium ricinoleate
5 parts of tall oil synergistic mixture-ethyl ester and
0.05 parts of 6-palmitoyl-ascorbate,
manufactured by precipitation of sodium ricinoleate with a solution of zinc and magnesium sulphate as well as addition of the hydroxylated tall oil esters of the antioxidant.

Active Substance Mixture I 95 parts of magnesium ricinoleate
5 parts of tall oil synergistic mixture as Mg salts and
0.1 parts of lauroyl-ascorbate,
manufactured by conjoint precipitation of the alkali salts from the castor oil acids and the hydroxylated tall oil acids and addition of the antioxidant.

Active Substance Mixture J 90 parts of magnesium ricinoleate
5 parts of abietic acid ethyl ester
0.1 parts of 6-palmitoyl-ascorbate, and
5 parts of trihydroxystearic acid ethyl ester,
manufactured by adding the esters and the antioxidant to the magnesium ricinoleate.

The following Examples illustrate the invention:

EXAMPLE 1 (Deodorant powder)

10 parts of active substance mixture A are ground and sieved to a particle size of less than 0.06 mm and added to a mixture of 80% of talc, 5% of rice starch and 5% of magnesium carbonate. A deodorising powder of excellent long-lasting action is produced.

EXAMPLE 2 (Deodorant cream)

10 parts of active substance mixture B are added to a mixture of the following components:
10 parts of stearic acid
22 parts of Lanette wax
18 parts of propylene glycol
10 parts of polywax p1 5 parts of isopropyl myristate and
25 parts of double distilled water.
The mass is stirred until cold. A deodorant cream of excellent long-lasting effect is produced.

EXAMPLE 3 (Deodorant dry spray)

50 parts of active substance mixtue C are mixed warm with 40 parts by weight of cetyl alcohol, 5 parts by weight of diisopropyl adipate and 5 parts by weight of isopropyl myristate. A stable dispersion is produced which can be processed with Frigen as the propellant gas to give a dry spray. A spray of this nature is outstandingly suitable for intimate cosmetic use because of its absolute nonirritant character.

EXAMPLE 4 (Deodorant cream)

A
  10.8 parts of stearic acid
  4.3 parts of isopropyl myristate
  0.1 parts of p-hydroxybenzoic acid propyl ester and
  4.5 parts of active substance mixture D
B
  50.5 parts of water
  0.1 parts of p-hydroxybenzoic acid methyl (?) ester
  0.4 parts of triethanolamine
  0.3 parts of 45% strength potassium hydroxide solution and
  5.4 parts of glycerine
C
  5.4 parts of glycerine monostearate and
  17.3 parts of water
A, B and C are prepared separately and subsequently mixed with one another.

EXAMPLE 5 (Deodorant stick)

32.0 parts of groundnut fat
9.0 parts of anti-sedimentation agent
20.0 parts of castor oil
10.0. parts of isopropyl palmitate
2.0 parts of carnauba wax
5.0 parts of lanoline
3.0 parts of beeswax
3.0 parts of solid skin-tolerated spreading agent
8.0 parts of hard paraffin
1.0 parts of antioxidant
6.0 parts of active substance mixture D and
1.0 parts of perfume oil

EXAMPLE 6 (Intimate spray)

28.0 parts of active substance mixture E
25.0 parts of skin-tolerated spreading agent (oil)
21.0 parts of isopropyl myristate
23.0 parts of oleyl oleate and
3.0 parts of perfume oil
100.0

Packaging:

6.0 parts of active substance mixture
37.6 parts of difluorodichloromethane and
56.4 parts of 1,1,2,2-tetrafluorodichloroethane

EXAMPLE 7 (Hair cream)

18.0 parts of fatty alcohol-wax ester mixture
13.5 parts of paraffin oil
4.5 parts of decanoltriglyceride
5.0 parts of active substance mixture F and
59.0 parts of water including perfume and preservatives

EXAMPLE 8 (Deodorant soap)

A
49.0 parts of base soap and
1.0 parts of perfume

B
25.0 parts of active substance mixture F and
25.0 parts of polywax 12,000

The base soap and perfume are milled; the active substance and polywax are fused at 90° C., cooled and also milled. Thereafter A and B are milled together.

EXAMPLE 9 (Skin milk)

A
5.0 parts of skin-tolerated spreading agent (oil)
17.0 parts of paraffin oil, 5° E.
2.0 parts of liquid lanoline
6.0 parts of isopropyl myristate
6.0 parts of trilauryl tetraglycol ether-o-phosphate
0.4 parts of triethanolamine and
10.0 parts of Active substance mixture F B
3.0 parts of glycerine
0.3 parts of carboxy-vinyl polymer
1.0 parts of preservative and
48.8 parts of water Warm A and B separately to about 70° C. Stir B into A at this temperature. Continue to stir until cold and perfume at about 40° C., thereafter homogenise.

EXAMPLE 10 (Foot fungus ointment)

30 parts of octyldodecanol
5.0 parts of paraffin 50°
15.0 parts of dimethylsulphoxide and
50.0 parts of active substance mixture G

EXAMPLE 11 (Powder for animal care)

40.0 parts of talc Ia
20.0 parts of rice starch
15.0 parts of China clay
10.0 parts of active substance mixture G
8.0 parts of zinc stearate
3.5 parts of zinc oxide and
3.5 parts of extremely fine silica gel

EXAMPLE 12 (Complete detergent with deodorising action)

15.0 parts of polypropylenebenzenesulphonate
5.0 parts of fatty alcohol polyglycol ether
5.0 parts of coconut fat soap
25.0 parts of sodium tripolyphosphate
8.0 parts of sodium orthophosphate
15.0 parts of sodium perborate
10.0 parts of sodium sulphate
5.0 parts of active substance mixture H
1.5 parts of carboxymethylcellulose
2.5 parts of magnesium silicate
0.3 parts of brightener and
7.7 parts of water

EXAMPLE 13 (Low odour polishing wax)

2 parts of synthetic wax O
4 parts of refined carnauba wax
2 parts of ozokerite keresine 64°/66°
15 parts of paraffin 50°/52° and
7 parts of active substance mixture I The base wax composition described above is fused and diluted with 70 parts of turpentine oil.

EXAMPLE 14 (Room spray for air improvement)

20.0 parts of active substance mixture J
30.0 parts of isopropyl myristate
10.0 parts of diisopropyl adipate
35.0 parts of isopropyl alcohol
4.5 parts of pine needle oil and
0.5 parts of butylhydroxytoluene 15 parts of the above mixture are packaged together with
42.5 parts of monofluorotrichloromethane and
42.5 parts of difluorodichloromethane.

EXAMPLE 15

In order to examine and compare the deodorising effect with hitherto usual active substances, two groups each of 15 test persons were compiled.

The first group each used a commercially available deodorant stick with hexachlorophene (a) as well as a deodorising cream (b) manufactured according to example 1, which was slightly perfumed. The deodorising effect of the two preparations was examined, for three different activities, by sensory perception at the armpits which had in each case been pre-treated in different ways as specified above. Result:

| (1) Sports activity in the open, light clothing | | |
|---|---|---|
| Examination after | a | b |
| 2 hours | 65% of the group completely deodorised | 100% of the group completely deodorised |
| 3 hours | 30% completely deodorised | 100% completely deodorised |

| (2) Normal day work (office work), closed clothing climatically controlled rooms (19° C.) | | |
|---|---|---|
| Examination after | a | b |
| 4 hours | 100% completely deodorised | 100% completely deodorised |
| 8 hours | 45% completely deodorised | 100% completely deodorised |
| 12 hours | 12% completely | 100% completely |

| | deodorised | deodorised |
|---|---|---|
| (3) Strenuous day work (warm factory spaces), closed protective clothing | | |
| Examination after | a | b |
| 2 hours | 40% completely deodorised | 100% completely deodorised |
| 4 hours | not deodorised | 100% completely deodorised |
| 8 hours | not deodorised | 80% completely deodorised |

The second group used a hexachlorophene-containing foot powder (a) for comparison, and on the other foot the powder (b) manufactured according to example 2, in order to examine the deodorising action against foot perspiration.

Footwear: water-tight rubber boots or rubber shoes. Stockings: wool socks, changed daily. Examination on 4 successive days, in each case after 3 hours and then after 8 hours. Results on all days agree for practical purposes:

| Examination after | a | b |
|---|---|---|
| 3 hours | 40–45% completely deodorised | 100% completely deodorised |
| 8 hours | 10–13% completely deodorised | 100% completely deodorised |

I claim:

1. A process for deodorizing a non-body odoriferous location which comprises contacting said location with a deodorizing amount of a compound which is a zinc salt of an unsaturated hydroxy-carboxylic acid having from 17 to 21 carbon atoms.

2. A process according to claim 1 wherein the carboxylic acid has 17 to 19 carbon atoms.

3. A process according to claim 2 wherein said carboxylic acid is ricinoleic acid.

4. A process according to claim 1 wherein the carboxylic acid is a member selected from the group consisting of ricinoleic acid and dihydroxyoctadecene acid.

5. A process according to claim 1 wherein said compound is zinc ricinoleate.

6. A process for deodorizing an odoriferous location which comprises contacting said location with a deodorizing amount of a compound which is a zinc salt of an unsaturated hydroxy-carboxylic acid having from 17 to 21 carbon atoms.

7. A process according to claim 6 wherein said zinc salt is zinc ricinoleate.

8. A process according to claim 7 wherein said zinc ricinoleate is present in a composition containing magnesium ricinoleate.

9. A process according to claim 6 wherein said zinc salt is present in a composition containing a partially hydrogenated phenanthrene derivative in an amount effective to favorably affect the odor suppressing action of said zinc salt.

10. A process according to claim 9 wherein said partially hydrogenated phenanthrene derivative is a salt of a carboxylic acid of a diterpene.

11. A process according to claim 10 wherein said phenanthrene derivative is a salt of abietic or laevopimaric acid present in said composition in an amount of from 1 to 30 percent by weight based on the weight of the composition.

12. A process according to claim 11 wherein said phenanthrene derivative is a magnesium, calcium or aluminum salt.

13. A process according to claim 11 wherein said phenanthrene derivative is a zinc salt.

14. A process according to claim 11 wherein said phenanthrene derivative is zinc abietate.

15. A process according to claim 9 wherein said composition further comprises an antioxidizing amount of an antioxidant.

16. A process according to claim 15 wherein said antioxidant is selected from the group consisting of ascorbic acid, 6-palmitoyl ascorbate, lauroyl-ascorbate and α-tocopherol.

17. A process according to claim 16 wherein said antioxidant is present in said composition in an amount of less than 1 percent by weight of the composition.

18. A process according to claim 17 wherein said antioxidant is present in said composition in amount of from 0.05 to 0.2 percent by weight of the composition.

19. A process according to claim 6 wherein said zinc salt is present in a composition containing a carrier therefor, said zinc salt being present in an amount between 0.5 and 20 percent by weight.

20. A process according to claim 6 wherein said zinc salt is present in a composition further comprising a reinforcing agent which is a hydroxy-carboxylic acid, an ester of a hydroxy-carboxylic acid or a salt of a hydroxy carboxylic acid wherein the carboxylic acid group has 13 to 21 carbon atoms, in an amount effective to reinforce the deodorizing effect of said zinc salt.

21. A process according to claim 20 wherein said reinforcing agent has 15–19 carbon atoms in the carboxylic acid group.

22. A process according to claim 20 wherein said reinforcing agent has 17–19 carbon atoms in the carboxylic acid group.

23. A process according to claim 22 wherein the acid moiety of said reinforcing agent is a member selected from the group consisting of di- tri- and tetrahydroxystearic acid and tri-hydroxy palmitic acid.

24. A process according to claim 23 wherein said reinforcing agent is a zinc salt.

25. A process according to claim 23 wherein said reinforcing agent is a magnesium salt.

26. A process according to claim 23 wherein said reinforcing agent is a calcium or aluminum salt.

27. A process according to claim 23 wherein said reinforcing agent is an ester of a monohydric alcohol.

28. A process according to claim 27 wherein said monohydric alcohol has 2-6 carbon atoms.

29. A process according to claim 23 wherein said reinforcing agent is present in said composition in an amount of 0.5 to 10% by weight of said composition.

30. A process according to claim 20 wherein said zinc salt and said reinforcing agent are present in a composition further comprising in anbioritizing amount of an antioxidant.

31. A process according to claim 30 wherein said antioxidant is selected from the group consisting of ascorbic acid, 6-palmitoyl ascorbate, lauroyl-ascorbate and α-tocopherol.

32. A process according to claim 31 wherein said anti-oxidant is present in said composition in an amount of less than 1 percent by weight, of the composition.

33. A process according to claim 32 wherein said antioxidant is present in said composition in an amount of from 0.05 to 0.2 percent by weight based on the total weight of active ingredients.

34. A process according to claim 30 wherein said composition further comprises a partially hydrogenated phenanthrene derivative in an amount effective to favorably affect the odor suppressing action of said zinc salt.

35. A process according to claim 34 wherein said partially hydrogenated phenanthrene derivative is a salt of a carboxylic acid of a diterpene.

36. A process according to claim 35 wherein said phenanthrene derivative is a salt of abietic or laevopimaric acid and is present in said composition in an amount of from 1 to 30 percent by weight of the composition.

37. A process according to claim 34 wherein said phenanthrene derivative is a zinc salt.

38. A process according to claim 37 wherein said phenanthrene derivative is zinc abietate.

39. A process according to claim 6 wherein said odoriferous location is on an animal or human.

40. A process according to claim 20, wherein said composition further comprises a partially hydrogenated phenanthrene derivative in an amount effective to favorably affect the odor suppressing action of said zinc salt.

41. A process according to claim 40, wherein said partially hydrogenated phenanthrene derivative is a salt of a carboxylic acid of a diterpene.

42. A process according to claim 41, wherein said phenanthrene derivative is a salt of abietic or laevopimaric acid present in said composition in an amount of from 1 to 30 percent by weight based on the weight of the composition.

43. A process according to claim 42, wherein said phenanthrene derivative is a magnesium, calcium or aluminum salt.

44. A process according to claim 42, wherein said phenanthrene derivative is a zinc salt.

45. A process according to claim 42, wherein said phenanthrene derivative is zinc abietate.

46. A process according to claim 6, said compound being present in a composition containing an antioxidizing amount of an antioxidant.

47. A deodorant composition comprising a deodorizing amount of a zinc salt of an unsaturated hydroxy-carboxylic acid having 17 to 21 carbon atoms and an antioxidizing amount of an antioxidant.

48. A deodorant composition according to claim 47 wherein said zinc salt is present in said composition in an amount of between 0.5 and 20 percent by weight.

49. A deodorant composition according to claim 47 wherein said zinc salt of an unsaturated hydroxy-carboxylic acid is zinc ricinoleate.

50. A deodorant composition comprising a deodorizing amount of a zinc salt of an unsaturated hydroxy-carboxylic acid having 17 to 21 carbon atoms, and a partially hydrogenated phenanthrene derivative in an amount effective to favorably affect the odor-suppressing action of said zinc salt.

51. A deodorant composition according to claim 50 wherein said partially hydrogenated phenanthrene derivative is a salt of a carboxylic acid of a diterpene.

52. A deodorant composition according to claim 51 wherein said phenanthrene derivative is a salt of abietic or laevopimaric acid and is present in said composition in an amount of from 1 to 30 percent by weight of the composition.

53. A deodorant composition according to claim 52 wherein said phenanthrene derivative is a magnesium, calcium or aluminum salt.

54. A deodorant composition according to claim 51 wherein said phenanthrene derivative is a zinc salt.

55. A deodorant composition according to claim 54 wherein said phenanthrene derivative is zinc abietate.

56. A deodorant composition according to claim 50 wherein said composition further comprises an antioxidizing amount of an antioxidant.

57. A deodorant composition according to claim 56 wherein said antioxidant is selected from the group consisting of ascorbic acid, 6-palmitoyl ascorbate, lauroyl-ascorbate and $\alpha$-tocopherol.

58. A deodorant composition according to claim 50 wherein said zinc salt of an unsaturated hydroxy-carboxylic acid is zinc ricinoleate.

59. A deodorant composition according to claim 50 wherein said zinc salt of an unsaturated hydroxy-carboxylic acid is zinc ricinoleate and said phenanthrene derivative is a salt or ester of abietic acid.

60. A deodorant composition according to claim 56 wherein said zinc salt of an unsaturated hydroxy-carboxylic acid is zinc ricinoleate.

61. A deodorant composition comprising a deodorizing amount of a zinc salt of an unsaturated hydroxy-carboxylic acid having 17 to 21 carbon atoms, and a reinforcing agent which is a hydroxy-carboxylic acid or a salt or ester of a hydroxy-carboxylic acid wherein the carboxylic acid group has 13 to 21 carbon atoms in an amount effective to reinforce the deodorizing effect of said zinc salt.

62. A deodorant composition according to claim 61 wherein said reinforcing agent has 15–19 carbon atoms in the carboxylic acid group.

63. A deodorant composition according to claim 62 wherein said reinforcing agent has 17–19 carbon atoms in the carboxylic acid group.

64. A deodorant composition according to claim 63 wherein the acid moiety of said reinforcing agent is a member selected from the group consisting of di- tri- and tetrahydroxystearic acid and tri-hydroxy palmitic acid.

65. A deodorant composition according to claim 64 wherein said reinforcing agent is a zinc salt.

66. A deodorant composition according to claim 65 wherein said reinforcing agent is a magnesium salt.

67. A deodorant composition according to claim 66 wherein said reinforcing agent is a calcium or aluminum salt.

68. A deodorant composition according to claim 61 wherein said reinforcing agent is an ester of a monohydric alcohol.

69. A deodorant composition according to claim 68 wherein said monohydric alcohol has 2–6 carbon atoms.

70. A deodorant composition according to claim 69 wherein said reinforcing agent is present in said composition in an amount of 0.5 to 10% by weight of the zinc salt plus reinforcing agent.

71. A deodorant composition according to claim 61 wherein said composition further comprises a antioxidizing amount of an antioxidant.

72. A deodorant composition according to claim 71 wherein said antioxidant is selected from the group consisting of ascorbic acid, 6-palmitoyl ascorbate, lauroyl-ascorbate and $\alpha$-tocopherol.

73. A deodorant composition according to claim 72 wherein said antioxidant is present in said composition in an amount of less than 1 percent by weight of the composition.

74. A deodorant composition according to claim 73 wherein said antioxidant is present in said composition in an amount of from 0.05 to 0.2 percent by weight of the composition.

75. A deodorant composition according to claim 71 wherein said composition further comprises a partially hydrogenated phenanthrene derivative in an amount effective to favorably affect the odor suppressing action of said zinc salt.

76. A deodorant composition according to claim 75 wherein said partially hydrogenated phenanthrene derivative is a salt of a carboxylic acid of a diterpene.

77. A deodorant composition according to claim 76 wherein said phenanthrene derivative is a salt of abietic or laevopimaric acid present in said composition in an amount of from 1 to 30 percent by weight of the composition.

78. A deodorant composition according to claim 61 further comprising a partially hydrogenated phenanthrene derivative in an amount effective to favorably affect the odor suppressing action of said zinc salt.

79. A deodorant composition according to claim 78 wherein said partially hydrogenated phenanthrene derivative is a salt of a carboxylic acid of a diterpene.

80. A deodorant composition according to claim 79 wherein said phenanthrene derivative is a salt of abietic or laevopimaric acid and is present in said composition in an amount of from 1 to 30 percent by weight of the composition.

81. A deodorant composition according to claim 80 wherein said phenanthrene derivative is a zinc salt.

82. A deodorant composition according to claim 81 wherein said phenanthrene derivative is zinc abietate.

* * * * *